(12) United States Patent
Asaka et al.

(10) Patent No.: US 10,457,711 B2
(45) Date of Patent: Oct. 29, 2019

(54) DERMATOPHAGOIDES FARINAE PROTEIN

(71) Applicant: TAIHO PHARMACEUTICAL CO., LTD., Chiyoda-ku (JP)

(72) Inventors: Naomasa Asaka, Tsukuba (JP); Yuki Tanaka, Tsukuba (JP); Naoki Inagaki, Gifu (JP)

(73) Assignee: TAIHO PHARMACEUTICAL CO., LTD., Chiyoda-ku (JP)

( * ) Notice: Subject to any disclaimer, the term of this patent is extended or adjusted under 35 U.S.C. 154(b) by 20 days.

(21) Appl. No.: 15/532,256

(22) PCT Filed: Dec. 1, 2015

(86) PCT No.: PCT/JP2015/083787
§ 371 (c)(1),
(2) Date: Jun. 1, 2017

(87) PCT Pub. No.: WO2016/088765
PCT Pub. Date: Jun. 9, 2016

(65) Prior Publication Data
US 2018/0265556 A1  Sep. 20, 2018

(30) Foreign Application Priority Data
Dec. 2, 2014 (JP) ................................. 2014-244038

(51) Int. Cl.
| C07K 14/43 | (2006.01) |
| --- | --- |
| A61K 39/35 | (2006.01) |
| C07K 14/435 | (2006.01) |
| C07K 16/18 | (2006.01) |
| C12N 15/09 | (2006.01) |
| G01N 33/53 | (2006.01) |
| A61K 49/00 | (2006.01) |
| A61K 38/00 | (2006.01) |

(52) U.S. Cl.
CPC ........ C07K 14/43563 (2013.01); A61K 39/35 (2013.01); A61K 49/0006 (2013.01); C07K 14/435 (2013.01); C07K 16/18 (2013.01); C12N 15/09 (2013.01); G01N 33/53 (2013.01); A61K 38/00 (2013.01)

(58) Field of Classification Search
CPC ............................ C07K 14/43563; A61K 39/35
See application file for complete search history.

(56) References Cited

U.S. PATENT DOCUMENTS

| 5,286,628 A | 2/1994 | Akagawa et al. | |
| --- | --- | --- | --- |
| 2003/0096779 A1 | 5/2003 | McCall et al. | |
| 2008/0038205 A1* | 2/2008 | McCall | C07K 14/43531 424/9.81 |
| 2008/0274059 A1* | 11/2008 | Moingeon | C07K 14/43531 424/9.81 |
| 2010/0024048 A1* | 1/2010 | Vazquez | A01K 67/033 800/8 |
| 2012/0289679 A1* | 11/2012 | Tsukui | A61K 39/35 530/324 |
| 2013/0157310 A1* | 6/2013 | Best | C07K 14/43531 435/69.3 |
| 2013/0280302 A1* | 10/2013 | Webster | A61K 9/0056 424/275.1 |
| 2014/0080997 A1* | 3/2014 | Tsukui | A61K 39/35 530/327 |

FOREIGN PATENT DOCUMENTS

| EP | 0 498 124 A1 | 8/1992 |
| --- | --- | --- |
| JP | 7-69925 A | 3/1995 |
| JP | 2002-512253 A | 4/2002 |
| JP | 2011-62098 A | 3/2011 |
| WO | 99/54349 A2 | 10/1999 |

OTHER PUBLICATIONS

An et al., 2013, Dermatophagoides farina Allergens Diversity Identification by Proteomics, Molecular & Cellular Proteomics, 12: 1818-1828.*
Gregoire et al., 2001, Recombinant Allergens, Clinical Reviews in Allergy and Immunology, 21: 215-227.*
International Search Report dated Mar. 1, 2016, in PCT/JP2015/083787, filed Dec. 1, 2015.
Korsgaard, "House-dust mites and asthma. A review on house-dust mites as a domestic risk factor for mite asthma", Allergy, vol. 53 (Suppl 48), 1998, p. 77-83.
Dilworth et al., "Sequence analysis of cDNA coding fora major house mite allergen, Der f I", Clinical and Experimental Allergy, vol. 21, 1991, 25-32.
Yuuki et al., "Cloning and Sequencing of cDNAS Corresponding to Mite Major Allergen Der f II", Jpn. J. Allergol., vol. 39, No. 6, 1990, p. 557-561.
Heymann et al., "Antigenic and structural analysis of group II allergens (Der f II and Der p II) from house dust mites (Dermatophagoides spp)", J. Allergy Clin. Immunol., vol. 83, No. 6, Jun. 1989, p. 1055-1067.

(Continued)

Primary Examiner — Amber D Steele
(74) Attorney, Agent, or Firm — Oblon, McClelland, Maier & Neustadt, L.L.P.

(57) ABSTRACT

Provided are a novel Dermatophagoides farinae protein, and a diagnostic drug, a prophylactic drug and a therapeutic drug for an allergic disease caused by Dermatophagoides farinae. A Dermatophagoides farinae protein selected from the group consisting of the following (a) to (c), or a fragment peptide thereof:
(a) a protein including an amino acid sequence set forth in SEQ ID NO:2;
(b) a protein including an amino acid sequence in which one or several amino acids have been substituted, deleted, or added relative to the amino acid sequence set forth in SEQ ID NO:2, and having allergenicity of Dermatophagoides farinae; and
(c) a protein including an amino acid sequence having 90% or higher identity with the amino acid sequence set forth in SEQ ID NO:2, and having allergenicity of Dermatophagoides farinae.

10 Claims, 3 Drawing Sheets
Specification includes a Sequence Listing.

(56) References Cited

OTHER PUBLICATIONS

Thomas et al., "Characterization and Immunobiology of House Mite Dust Allergens", Int. Arch. Allergy immunology, vol. 129, 2002, p. 1-18.
Extended European Search Report dated Mar. 20, 2018 in European Patent Application No. 15864977.2, citing documents AO, and AU through AX therein, 9 pages.
Asturias, J. A., et al., "Engineering of Major House Dust Mite Allergens Der p 1 and Der p 2 for Allergen-Specific Immunotherapy", Clinical & Experimental Allergy, XP055168215, vol. 39 No. 7, Jul. 1, 2009, pp. 1088-1098.
Chen, K. W., et al., "Carrier-bound Nonallergenic Der p 2 Peptides Induce IgG Antibodies Blocking Allergen-Induced Basophil Activation in Allergic Patients", Allergy, XP055039011, vol. 67, No. 5, May 1, 2012, pp. 609-621.
Fujikawa, A., et al., "Cloning and Characterization of a New Allergen. Mag 3, from the House Dust Mite, Dermatophagoides Farinae: Cross-Reactivity with High-Molecular-Weight Allergen", Molecular Immunology, XP002113314, vol. 33 No. 3, Jan. 1, 1996, pp. 311-319.
Tanabe, S., "Epitope Peptides and Immunotherapy", Current Protein and Peptide Science. XP008098245, vol. 8 No. 1, Feb. 1, 2007, pp. 109-118.
Office Action dated Dec. 12, 2017 in Japanese Patent Application No. 2016-562641 (with partial English translation).
Su An, et al., "Dematophagoides farinae Allergens Diversity Identification by Proteomics", Molecular & Cellular Proteomics, The American Society for Biochemistry and Molecular Biology, Vo. 12, 2013, pp. 1818-1828.
Noguchi E., et al., "Comparisons of IgE, IgG, and IgG4 responsiveness to Dermatophagoides farinae in children by immunoblotting", ALLERGY, vol. 51, 1996, pp. 907-913.

* cited by examiner

SEQUENCE LISTING

<160> NUMBER OF SEQ ID NOS: 15

<210> SEQ ID NO 1
<211> LENGTH: 3006
<212> TYPE: DNA

```
<213> ORGANISM: Dermatophagoides Farinae
<220> FEATURE:
<221> NAME/KEY: CDS
<222> LOCATION: (1)..(3006)
<220> FEATURE:
<221> NAME/KEY: sig_peptide
<222> LOCATION: (1)..(81)
<220> FEATURE:
<221> NAME/KEY: mat_peptide
<222> LOCATION: (82)..(3006)

<400> SEQUENCE: 1
```

| | | | | | | | | | | | | | | | | |
|---|---|---|---|---|---|---|---|---|---|---|---|---|---|---|---|---|
| atg | tat | cat | aat | cta | tca | tta | ttg | gtg | gtg | gct | cta | ttg | tct | gtg | | 48 |
| Met | Asp | Tyr | His | Asn | Leu | Ser | Leu | Leu | Val | Val | Ala | Leu | Leu | Ser | Val | |
| | | -25 | | | | -20 | | | | | -15 | | | | | |
| acc | ata | ttc | aca | aca | att | caa | caa | tct | gaa | tcg | gtt | gtt | att | aaa | gtg | 96 |
| Thr | Ile | Phe | Thr | Thr | Ile | Gln | Gln | Ser | Glu | Ser | Val | Val | Ile | Lys | Val | |
| | -10 | | | | | -5 | | | | -1 | 1 | | | | 5 | |
| gaa | aat | ctg | cca | gaa | cgt | tgt | gat | tat | tca | caa | tgt | cca | aaa | tgg | gat | 144 |
| Glu | Asn | Leu | Pro | Glu | Arg | Cys | Asp | Tyr | Ser | Gln | Cys | Pro | Lys | Trp | Asp | |
| | | | | 10 | | | | | 15 | | | | | 20 | | |
| cct | aat | gat | att | aat | gta | cat | ttg | gtg | gcc | cat | aca | cat | gat | gat | gtt | 192 |
| Pro | Asn | Asp | Ile | Asn | Val | His | Leu | Val | Ala | His | Thr | His | Asp | Asp | Val | |
| | | | 25 | | | | | 30 | | | | | 35 | | | |
| ggt | tgg | tta | aaa | acg | gtg | gaa | caa | tat | tat | tat | ggc | cta | aaa | aat | gat | 240 |
| Gly | Trp | Leu | Lys | Thr | Val | Glu | Gln | Tyr | Tyr | Tyr | Gly | Leu | Lys | Asn | Asp | |
| | | 40 | | | | | 45 | | | | | 50 | | | | |
| att | caa | cgt | gcc | gga | gtg | caa | tat | att | ttg | gat | aca | gta | att | gaa | gaa | 288 |
| Ile | Gln | Arg | Ala | Gly | Val | Gln | Tyr | Ile | Leu | Asp | Thr | Val | Ile | Glu | Glu | |
| | 55 | | | | | 60 | | | | | 65 | | | | | |
| tta | ata | cgt | aat | aaa | caa | cga | cgt | ttt | att | tat | gtt | gag | att | gca | ttc | 336 |
| Leu | Ile | Arg | Asn | Lys | Gln | Arg | Arg | Phe | Ile | Tyr | Val | Glu | Ile | Ala | Phe | |
| 70 | | | | | 75 | | | | | 80 | | | | | 85 | |
| ttt | tgg | aaa | tgg | tgg | caa | gaa | caa | gat | gaa | gat | caa | cgt | atg | atc | gta | 384 |
| Phe | Trp | Lys | Trp | Trp | Gln | Glu | Gln | Asp | Glu | Asp | Gln | Arg | Met | Ile | Val | |
| | | | | 90 | | | | | 95 | | | | | 100 | | |
| cga | gaa | tta | gta | cgt | act | gga | caa | ttg | gaa | ttt | att | aat | ggt | ggc | tgg | 432 |
| Arg | Glu | Leu | Val | Arg | Thr | Gly | Gln | Leu | Glu | Phe | Ile | Asn | Gly | Gly | Trp | |
| | | | 105 | | | | | 110 | | | | | 115 | | | |
| tca | atg | cca | gat | gaa | gca | gca | aca | cat | tat | aat | tca | ctt | att | gat | caa | 480 |
| Ser | Met | Pro | Asp | Glu | Ala | Ala | Thr | His | Tyr | Asn | Ser | Leu | Ile | Asp | Gln | |
| | | 120 | | | | | 125 | | | | | 130 | | | | |
| tct | aca | tgg | ggt | cta | aga | caa | ttg | aat | gat | aca | ttc | ggt | aaa | tgt | ggt | 528 |
| Ser | Thr | Trp | Gly | Leu | Arg | Gln | Leu | Asn | Asp | Thr | Phe | Gly | Lys | Cys | Gly | |
| | 135 | | | | | 140 | | | | | 145 | | | | | |
| cat | cca | aaa | gta | aca | tgg | caa | att | gat | cca | ttt | ggt | cat | tcc | cgg | gaa | 576 |
| His | Pro | Lys | Val | Thr | Trp | Gln | Ile | Asp | Pro | Phe | Gly | His | Ser | Arg | Glu | |
| 150 | | | | | 155 | | | | | 160 | | | | | 165 | |
| atg | gct | aat | ctt | tat | gca | cag | atg | ggt | tat | gat | gca | tta | ttt | ttt | gca | 624 |
| Met | Ala | Asn | Leu | Tyr | Ala | Gln | Met | Gly | Tyr | Asp | Ala | Leu | Phe | Phe | Ala | |
| | | | | 170 | | | | | 175 | | | | | 180 | | |
| cgt | caa | gat | tat | caa | gat | cgt | gaa | aat | cgt | atg | aca | aat | cgt | aaa | ttg | 672 |
| Arg | Gln | Asp | Tyr | Gln | Asp | Arg | Glu | Asn | Arg | Met | Thr | Asn | Arg | Lys | Leu | |
| | | | 185 | | | | | 190 | | | | | 195 | | | |
| gaa | cat | gta | tgg | caa | gga | tca | gat | gat | ctt | ggt | act | gct | ggt | gat | ata | 720 |
| Glu | His | Val | Trp | Gln | Gly | Ser | Asp | Asp | Leu | Gly | Thr | Ala | Gly | Asp | Ile | |
| | | 200 | | | | | 205 | | | | | 210 | | | | |
| ttc | act | ggt | atg | atg | ttt | agt | ggt | tat | gga | cct | att | gaa | ttc | aat | tgg | 768 |
| Phe | Thr | Gly | Met | Met | Phe | Ser | Gly | Tyr | Gly | Pro | Ile | Glu | Phe | Asn | Trp | |
| | 215 | | | | | 220 | | | | | 225 | | | | | |
| gat | ata | aca | aat | ggc | ccc | gaa | gat | gct | gtt | gtt | gat | aat | cct | gag | tca | 816 |
| Asp | Ile | Thr | Asn | Gly | Pro | Glu | Asp | Ala | Val | Val | Asp | Asn | Pro | Glu | Ser | |

```
      230                 235                 240                 245
gaa gaa tat aat gtt ccg gat aaa ata cga cgt ttt gtg gaa aaa gca            864
Glu Glu Tyr Asn Val Pro Asp Lys Ile Arg Arg Phe Val Glu Lys Ala
                250                 255                 260 aaa tat ttt gca cag tat tat gca aca aat cat ttt atg ttt cca atg            912
Lys Tyr Phe Ala Gln Tyr Tyr Ala Thr Asn His Phe Met Phe Pro Met
            265                 270                 275 ggt acg gat ttt caa tat ggt gat gca cat aca tgg ttt aaa aat ctg            960
Gly Thr Asp Phe Gln Tyr Gly Asp Ala His Thr Trp Phe Lys Asn Leu
        280                 285                 290 gat aaa ttg atc aaa gct gta aat aat gct gga aaa ggt gtt cgg gca           1008
Asp Lys Leu Ile Lys Ala Val Asn Asn Ala Gly Lys Gly Val Arg Ala
    295                 300                 305 ttc tat tca aca cca tca tgc tat gca cgt gca tta tat gaa acg aat           1056
Phe Tyr Ser Thr Pro Ser Cys Tyr Ala Arg Ala Leu Tyr Glu Thr Asn
310                 315                 320                 325 cgt aca tgg acc acg aaa aca gat gat ttt ttt ccc tat gca tca gat           1104
Arg Thr Trp Thr Thr Lys Thr Asp Asp Phe Phe Pro Tyr Ala Ser Asp
                330                 335                 340 gaa cat gca tat tgg act gga tat ttc acc agt aga ccg gct tta aaa           1152
Glu His Ala Tyr Trp Thr Gly Tyr Phe Thr Ser Arg Pro Ala Leu Lys
            345                 350                 355 cgt atg gaa cgt atg ggc aat aat cta tta caa gca tgt aaa caa ttg           1200
Arg Met Glu Arg Met Gly Asn Asn Leu Leu Gln Ala Cys Lys Gln Leu
        360                 365                 370 gat att ttg gcc gga aat gat gga cgt ttt gaa atg aat ata aca aga           1248
Asp Ile Leu Ala Gly Asn Asp Gly Arg Phe Glu Met Asn Ile Thr Arg
    375                 380                 385 tta cgt gaa gca atg ggt gtc atg caa cat cat gat gct gta acc gga           1296
Leu Arg Glu Ala Met Gly Val Met Gln His His Asp Ala Val Thr Gly
390                 395                 400                 405 acg gaa aaa caa cat gtt gca ttt aat tat gca aaa atg tta gat tca           1344
Thr Glu Lys Gln His Val Ala Phe Asn Tyr Ala Lys Met Leu Asp Ser
                410                 415                 420 gca atg cta caa tgt cgt cat gta att agt gaa tca tat cga aag tta           1392
Ala Met Leu Gln Cys Arg His Val Ile Ser Glu Ser Tyr Arg Lys Leu
            425                 430                 435 ttt cca aca caa aca aaa gaa cag cat gaa ttt tgt cca tat tta aat           1440
Phe Pro Thr Gln Thr Lys Glu Gln His Glu Phe Cys Pro Tyr Leu Asn
        440                 445                 450 ata agt tca tgt cct tca aca gaa atg ggt gaa tca cgt acg ata cat           1488
Ile Ser Ser Cys Pro Ser Thr Glu Met Gly Glu Ser Arg Thr Ile His
    455                 460                 465 ctt tat aat cca ctt ggt cat cgt tta gtg aat cga aca ata cgt gta           1536
Leu Tyr Asn Pro Leu Gly His Arg Leu Val Asn Arg Thr Ile Arg Val
470                 475                 480                 485 cct gta aag gat ggt tat tat tat caa gtt cgt gac caa aat gat cat           1584
Pro Val Lys Asp Gly Tyr Tyr Tyr Gln Val Arg Asp Gln Asn Asp His
                490                 495                 500 tca ata cct gct gtt ttg ata tca ata cca gaa ttt gtt cgt aaa att           1632
Ser Ile Pro Ala Val Leu Ile Ser Ile Pro Glu Phe Val Arg Lys Ile
            505                 510                 515 cct gga cgt aaa agt gtg gcc aca aaa gaa tta gta ttc cgt gta cct           1680
Pro Gly Arg Lys Ser Val Ala Thr Lys Glu Leu Val Phe Arg Val Pro
        520                 525                 530 att att gaa tca ctt ggt ata cgt aga ttt cat atg att gcc act aaa           1728
Ile Ile Glu Ser Leu Gly Ile Arg Arg Phe His Met Ile Ala Thr Lys
    535                 540                 545 gaa aaa caa cag gat tca gct gtt gaa atc caa gga gaa aaa ttt gtt           1776
```

-continued

| | | | | | | | | | | | | | | |
|---|---|---|---|---|---|---|---|---|---|---|---|---|---|---|
| | Glu | Lys | Gln | Gln | Asp | Ser | Ala | Val | Glu | Ile | Gln | Gly | Glu | Lys | Phe | Val |
| | 550 | | | | 555 | | | | 560 | | | | 565 | | |

| ggt | cat | aaa | gga | caa | cga | ttt | caa | ctt | aaa | gat | ggt | ttg | att | att | gaa | 1824 |
|---|---|---|---|---|---|---|---|---|---|---|---|---|---|---|---|---|
| Gly | His | Lys | Gly | Gln | Arg | Phe | Gln | Leu | Lys | Asp | Gly | Leu | Ile | Ile | Glu | |
| | | | | 570 | | | | 575 | | | | 580 | | | | |

| ttt | gat | tct | aat | gga | aaa | att | gca | aca | atg | act | cga | aat | aat | caa | tcg | 1872 |
|---|---|---|---|---|---|---|---|---|---|---|---|---|---|---|---|---|
| Phe | Asp | Ser | Asn | Gly | Lys | Ile | Ala | Thr | Met | Thr | Arg | Asn | Asn | Gln | Ser | |
| | | | 585 | | | | | 590 | | | | | 595 | | | |

| ata | tcg | ata | tcg | aat | gaa | ttc | cgt | ttg | ttt | cat | ggt | gct | gat | att | ggt | 1920 |
|---|---|---|---|---|---|---|---|---|---|---|---|---|---|---|---|---|
| Ile | Ser | Ile | Ser | Asn | Glu | Phe | Arg | Leu | Phe | His | Gly | Ala | Asp | Ile | Gly | |
| | | | 600 | | | | | 605 | | | | | 610 | | | |

| cgt | cat | tca | ggt | gcc | tat | att | ttc | cgt | cca | agt | gaa | cag | aaa | act | ttt | 1968 |
|---|---|---|---|---|---|---|---|---|---|---|---|---|---|---|---|---|
| Arg | His | Ser | Gly | Ala | Tyr | Ile | Phe | Arg | Pro | Ser | Glu | Gln | Lys | Thr | Phe | |
| | 615 | | | | | 620 | | | | | 625 | | | | | |

| cct | gtc | aca | gaa | aaa | atg | gaa | gca | aca | ttg | tat | gta | gat | caa | aaa | ttc | 2016 |
|---|---|---|---|---|---|---|---|---|---|---|---|---|---|---|---|---|
| Pro | Val | Thr | Glu | Lys | Met | Glu | Ala | Thr | Leu | Tyr | Val | Asp | Gln | Lys | Phe | |
| 630 | | | | | 635 | | | | | 640 | | | | | 645 | |

| ggt | atc | gtt | caa | gaa | gta | cat | caa | caa | ttt | gat | tca | ttt | gtt | ggt | caa | 2064 |
|---|---|---|---|---|---|---|---|---|---|---|---|---|---|---|---|---|
| Gly | Ile | Val | Gln | Glu | Val | His | Gln | Gln | Phe | Asp | Ser | Phe | Val | Gly | Gln | |
| | | | | 650 | | | | | 655 | | | | | 660 | | |

| atc | ata | cga | ttg | gat | aaa | caa | ggt | gat | tat | gtg | gaa | ttt | gat | ttt | gtt | 2112 |
|---|---|---|---|---|---|---|---|---|---|---|---|---|---|---|---|---|
| Ile | Ile | Arg | Leu | Asp | Lys | Gln | Gly | Asp | Tyr | Val | Glu | Phe | Asp | Phe | Val | |
| | | | 665 | | | | | 670 | | | | | 675 | | | |

| gtt | gga | cca | att | cca | gtg | gat | gat | cta | att | ggt | aaa | gaa | atc | att | aca | 2160 |
|---|---|---|---|---|---|---|---|---|---|---|---|---|---|---|---|---|
| Val | Gly | Pro | Ile | Pro | Val | Asp | Asp | Leu | Ile | Gly | Lys | Glu | Ile | Ile | Thr | |
| | | 680 | | | | | 685 | | | | | 690 | | | | |

| cga | tat | agt | acg | aat | ctt | gca | aat | gat | gaa | aca | ttc | ttt | acc | gat | tca | 2208 |
|---|---|---|---|---|---|---|---|---|---|---|---|---|---|---|---|---|
| Arg | Tyr | Ser | Thr | Asn | Leu | Ala | Asn | Asp | Glu | Thr | Phe | Phe | Thr | Asp | Ser | |
| | 695 | | | | | 700 | | | | | 705 | | | | | |

| aat | ggt | cga | caa | atg | tta | cga | aga | cgt | tgg | aat | tat | cgt | cca | tca | tgg | 2256 |
|---|---|---|---|---|---|---|---|---|---|---|---|---|---|---|---|---|
| Asn | Gly | Arg | Gln | Met | Leu | Arg | Arg | Arg | Trp | Asn | Tyr | Arg | Pro | Ser | Trp | |
| 710 | | | | | 715 | | | | | 720 | | | | | 725 | |

| aaa | tat | gaa | atc | gaa | gaa | cca | gta | tcg | ggt | aat | tat | tat | ccg | gtt | aat | 2304 |
|---|---|---|---|---|---|---|---|---|---|---|---|---|---|---|---|---|
| Lys | Tyr | Glu | Ile | Glu | Glu | Pro | Val | Ser | Gly | Asn | Tyr | Tyr | Pro | Val | Asn | |
| | | | | 730 | | | | | 735 | | | | | 740 | | |

| tca | cgt | att | gct | att | cgt | gat | gat | aga | aaa | tca | ttg | cag | atg | aca | att | 2352 |
|---|---|---|---|---|---|---|---|---|---|---|---|---|---|---|---|---|
| Ser | Arg | Ile | Ala | Ile | Arg | Asp | Asp | Arg | Lys | Ser | Leu | Gln | Met | Thr | Ile | |
| | | | 745 | | | | | 750 | | | | | 755 | | | |

| atg | act | gat | cga | tca | caa | ggt | ggt | tca | tta | tca | cct | gaa | caa | att | aat | 2400 |
|---|---|---|---|---|---|---|---|---|---|---|---|---|---|---|---|---|
| Met | Thr | Asp | Arg | Ser | Gln | Gly | Gly | Ser | Leu | Ser | Pro | Glu | Gln | Ile | Asn | |
| | | | 760 | | | | | 765 | | | | | 770 | | | |

| ggc | agc | gtt | gat | cta | atg | gta | cat | cgt | cgt | tta | tta | cat | gat | gat | tat | 2448 |
|---|---|---|---|---|---|---|---|---|---|---|---|---|---|---|---|---|
| Gly | Ser | Val | Asp | Leu | Met | Val | His | Arg | Arg | Leu | Leu | His | Asp | Asp | Tyr | |
| | 775 | | | | | 780 | | | | | 785 | | | | | |

| ttt | ggt | gtc | gat | gaa | cca | tta | aat | gaa | cca | ggt | gtt | gat | ggt | cat | ggc | 2496 |
|---|---|---|---|---|---|---|---|---|---|---|---|---|---|---|---|---|
| Phe | Gly | Val | Asp | Glu | Pro | Leu | Asn | Glu | Pro | Gly | Val | Asp | Gly | His | Gly | |
| 790 | | | | | 795 | | | | | 800 | | | | | 805 | |

| ata | gtt | ata | cgt | ggc | aga | cat | tta | tta | cta | tta | gat | aca | ttg | gaa | aaa | 2544 |
|---|---|---|---|---|---|---|---|---|---|---|---|---|---|---|---|---|
| Ile | Val | Ile | Arg | Gly | Arg | His | Leu | Leu | Leu | Leu | Asp | Thr | Leu | Glu | Lys | |
| | | | 810 | | | | | 815 | | | | | 820 | | | |

| gct | gcc | gaa | aaa | cat | cgt | cca | ctt | gca | cag | gaa | atg | ttt | atg | gag | cca | 2592 |
|---|---|---|---|---|---|---|---|---|---|---|---|---|---|---|---|---|
| Ala | Ala | Glu | Lys | His | Arg | Pro | Leu | Ala | Gln | Glu | Met | Phe | Met | Glu | Pro | |
| | | | 825 | | | | | 830 | | | | | 835 | | | |

| att | att | agt | ttt | aca | tca | tcg | atg | gag | aaa | aat | cag | cca | ata | tat | aag | 2640 |
|---|---|---|---|---|---|---|---|---|---|---|---|---|---|---|---|---|
| Ile | Ile | Ser | Phe | Thr | Ser | Ser | Met | Glu | Lys | Asn | Gln | Pro | Ile | Tyr | Lys | |
| | | | 840 | | | | | 845 | | | | | 850 | | | |

| gga | tta | acg | aaa | gat | ctg | cct | gga | aat | gtt | cat | ctt | ctt | acc | ctg | gaa | 2688 |
|---|---|---|---|---|---|---|---|---|---|---|---|---|---|---|---|---|
| Gly | Leu | Thr | Lys | Asp | Leu | Pro | Gly | Asn | Val | His | Leu | Leu | Thr | Leu | Glu | |
| 855 | | | | | 860 | | | | | 865 | | | | | | |

-continued

| | |
|---|---|
| caa tgg cat tca aaa cgt tat cta tta cgt ctt gaa cat ttt tat caa<br>Gln Trp His Ser Lys Arg Tyr Leu Leu Arg Leu Glu His Phe Tyr Gln<br>870               875                   880               885 | 2736 |
| cgt ttt gaa gat cca tca ttg agt aat cca gcc act gta tcg tta cgc<br>Arg Phe Glu Asp Pro Ser Leu Ser Asn Pro Ala Thr Val Ser Leu Arg<br>               890                   895                   900 | 2784 |
| cat tta ttt caa tca ttt gaa ata act gcc gtt gaa gaa tta acg ctt<br>His Leu Phe Gln Ser Phe Glu Ile Thr Ala Val Glu Glu Leu Thr Leu<br>           905                   910                   915 | 2832 |
| ggt gca aat caa ccg ata tca gcg ttg aaa aat cgt tta caa tat cgt<br>Gly Ala Asn Gln Pro Ile Ser Ala Leu Lys Asn Arg Leu Gln Tyr Arg<br>920               925                   930 | 2880 |
| tat att aga cca tta aat gag caa caa tca tcg atc ata acg gat cca<br>Tyr Ile Arg Pro Leu Asn Glu Gln Gln Ser Ser Ile Ile Thr Asp Pro<br>           935                   940                   945 | 2928 |
| ata att gaa ggt gaa aat ttc gat att cat ctt gaa ccg atg cag ata<br>Ile Ile Glu Gly Glu Asn Phe Asp Ile His Leu Glu Pro Met Gln Ile<br>950               955                   960               965 | 2976 |
| cgt aca ttt tta atc gat att aaa cga aat<br>Arg Thr Phe Leu Ile Asp Ile Lys Arg Asn<br>           970                   975 | 3006 |

<210> SEQ ID NO 2
<211> LENGTH: 1002
<212> TYPE: PRT
<213> ORGANISM: Dermatophagoides Farinae

<400> SEQUENCE: 2

Met Asp Tyr His Asn Leu Ser Leu Leu Val Val Ala Leu Leu Ser Val
           -25                   -20                       -15

Thr Ile Phe Thr Thr Ile Gln Gln Ser Glu Ser Val Val Ile Lys Val
           -10                   -5                  -1  1                5

Glu Asn Leu Pro Glu Arg Cys Asp Tyr Ser Gln Cys Pro Lys Trp Asp
                  10                       15                    20

Pro Asn Asp Ile Asn Val His Leu Val Ala His Thr His Asp Asp Val
             25                   30                   35

Gly Trp Leu Lys Thr Val Glu Gln Tyr Tyr Gly Leu Lys Asn Asp
   40                       45                   50

Ile Gln Arg Ala Gly Val Gln Tyr Ile Leu Asp Thr Val Ile Glu Glu
    55                    60                   65

Leu Ile Arg Asn Lys Gln Arg Arg Phe Ile Tyr Val Glu Ile Ala Phe
70               75                   80               85

Phe Trp Lys Trp Trp Gln Glu Gln Asp Glu Asp Gln Arg Met Ile Val
             90                   95                 100

Arg Glu Leu Val Arg Thr Gly Gln Leu Glu Phe Ile Asn Gly Gly Trp
         105                    110                   115

Ser Met Pro Asp Glu Ala Ala Thr His Tyr Asn Ser Leu Ile Asp Gln
        120                    125                 130

Ser Thr Trp Gly Leu Arg Gln Leu Asn Asp Thr Phe Gly Lys Cys Gly
     135                  140                  145

His Pro Lys Val Thr Trp Gln Ile Asp Pro Phe Gly His Ser Arg Glu
150             155                 160               165

Met Ala Asn Leu Tyr Ala Gln Met Gly Tyr Asp Ala Leu Phe Phe Ala
                  170                   175               180

Arg Gln Asp Tyr Gln Asp Arg Glu Asn Arg Met Thr Asn Arg Lys Leu
             185                    190                195

Glu His Val Trp Gln Gly Ser Asp Asp Leu Gly Thr Ala Gly Asp Ile

```
              200                 205                 210
Phe Thr Gly Met Met Phe Ser Gly Tyr Gly Pro Ile Glu Phe Asn Trp
215                 220                 225

Asp Ile Thr Asn Gly Pro Glu Asp Ala Val Val Asp Asn Pro Glu Ser
230                 235                 240                 245

Glu Glu Tyr Asn Val Pro Asp Lys Ile Arg Arg Phe Val Glu Lys Ala
                250                 255                 260

Lys Tyr Phe Ala Gln Tyr Ala Thr Asn His Phe Met Phe Pro Met
            265                 270                 275

Gly Thr Asp Phe Gln Tyr Gly Asp Ala His Thr Trp Phe Lys Asn Leu
        280                 285                 290

Asp Lys Leu Ile Lys Ala Val Asn Asn Ala Gly Lys Gly Val Arg Ala
        295                 300                 305

Phe Tyr Ser Thr Pro Ser Cys Tyr Ala Arg Ala Leu Tyr Glu Thr Asn
310                 315                 320                 325

Arg Thr Trp Thr Thr Lys Thr Asp Asp Phe Phe Pro Tyr Ala Ser Asp
                330                 335                 340

Glu His Ala Tyr Trp Thr Gly Tyr Phe Thr Ser Arg Pro Ala Leu Lys
            345                 350                 355

Arg Met Glu Arg Met Gly Asn Asn Leu Leu Gln Ala Cys Lys Gln Leu
            360                 365                 370

Asp Ile Leu Ala Gly Asn Asp Gly Arg Phe Glu Met Asn Ile Thr Arg
        375                 380                 385

Leu Arg Glu Ala Met Gly Val Met Gln His His Asp Ala Val Thr Gly
390                 395                 400                 405

Thr Glu Lys Gln His Val Ala Phe Asn Tyr Ala Lys Met Leu Asp Ser
                410                 415                 420

Ala Met Leu Gln Cys Arg His Val Ile Ser Glu Ser Tyr Arg Lys Leu
            425                 430                 435

Phe Pro Thr Gln Thr Lys Glu Gln His Glu Phe Cys Pro Tyr Leu Asn
        440                 445                 450

Ile Ser Ser Cys Pro Ser Thr Glu Met Gly Glu Ser Arg Thr Ile His
        455                 460                 465

Leu Tyr Asn Pro Leu Gly His Arg Leu Val Asn Arg Thr Ile Arg Val
470                 475                 480                 485

Pro Val Lys Asp Gly Tyr Tyr Tyr Gln Val Arg Asp Gln Asn Asp His
                490                 495                 500

Ser Ile Pro Ala Val Leu Ile Ser Ile Pro Glu Phe Val Arg Lys Ile
            505                 510                 515

Pro Gly Arg Lys Ser Val Ala Thr Lys Glu Leu Val Phe Arg Val Pro
        520                 525                 530

Ile Ile Glu Ser Leu Gly Ile Arg Arg Phe His Met Ile Ala Thr Lys
        535                 540                 545

Glu Lys Gln Gln Asp Ser Ala Val Glu Ile Gln Gly Glu Lys Phe Val
550                 555                 560                 565

Gly His Lys Gly Gln Arg Phe Gln Leu Lys Asp Gly Leu Ile Ile Glu
                570                 575                 580

Phe Asp Ser Asn Gly Lys Ile Ala Thr Met Thr Arg Asn Asn Gln Ser
            585                 590                 595

Ile Ser Ile Ser Asn Glu Phe Arg Leu Phe His Gly Ala Asp Ile Gly
        600                 605                 610

Arg His Ser Gly Ala Tyr Ile Phe Arg Pro Ser Glu Gln Lys Thr Phe
        615                 620                 625
```

```
Pro Val Thr Glu Lys Met Glu Ala Thr Leu Tyr Val Asp Gln Lys Phe
630                 635                 640                 645

Gly Ile Val Gln Glu Val His Gln Gln Phe Asp Ser Phe Val Gly Gln
            650                 655                 660

Ile Ile Arg Leu Asp Lys Gln Gly Asp Tyr Val Glu Phe Asp Phe Val
            665                 670                 675

Val Gly Pro Ile Pro Val Asp Asp Leu Ile Gly Lys Glu Ile Ile Thr
            680                 685                 690

Arg Tyr Ser Thr Asn Leu Ala Asn Asp Glu Thr Phe Phe Thr Asp Ser
            695                 700                 705

Asn Gly Arg Gln Met Leu Arg Arg Arg Trp Asn Tyr Arg Pro Ser Trp
710                 715                 720                 725

Lys Tyr Glu Ile Glu Glu Pro Val Ser Gly Asn Tyr Tyr Pro Val Asn
                730                 735                 740

Ser Arg Ile Ala Ile Arg Asp Asp Arg Lys Ser Leu Gln Met Thr Ile
            745                 750                 755

Met Thr Asp Arg Ser Gln Gly Gly Ser Leu Ser Pro Glu Gln Ile Asn
            760                 765                 770

Gly Ser Val Asp Leu Met Val His Arg Leu Leu His Asp Asp Asp Tyr
775                 780                 785

Phe Gly Val Asp Glu Pro Leu Asn Glu Pro Gly Val Asp Gly His Gly
790                 795                 800                 805

Ile Val Ile Arg Gly Arg His Leu Leu Leu Leu Asp Thr Leu Glu Lys
            810                 815                 820

Ala Ala Glu Lys His Arg Pro Leu Ala Gln Met Phe Met Glu Pro
            825                 830                 835

Ile Ile Ser Phe Thr Ser Ser Met Glu Lys Asn Gln Pro Ile Tyr Lys
            840                 845                 850

Gly Leu Thr Lys Asp Leu Pro Gly Asn Val His Leu Leu Thr Leu Glu
855                 860                 865

Gln Trp His Ser Lys Arg Tyr Leu Leu Arg Leu Glu His Phe Tyr Gln
870                 875                 880                 885

Arg Phe Glu Asp Pro Ser Leu Ser Asn Pro Ala Thr Val Ser Leu Arg
                890                 895                 900

His Leu Phe Gln Ser Phe Glu Ile Thr Ala Val Glu Glu Leu Thr Leu
            905                 910                 915

Gly Ala Asn Gln Pro Ile Ser Ala Leu Lys Asn Arg Leu Gln Tyr Arg
            920                 925                 930

Tyr Ile Arg Pro Leu Asn Glu Gln Gln Ser Ser Ile Ile Thr Asp Pro
            935                 940                 945

Ile Ile Glu Gly Glu Asn Phe Asp Ile His Leu Glu Pro Met Gln Ile
950                 955                 960                 965

Arg Thr Phe Leu Ile Asp Ile Lys Arg Asn
                970                 975

<210> SEQ ID NO 3
<211> LENGTH: 20
<212> TYPE: PRT
<213> ORGANISM: Dermatophagoides Farinae

<400> SEQUENCE: 3

Thr Asp Asp Phe Phe Pro Tyr Ala Ser Asp Glu His Ala Tyr Trp Thr
1               5                   10                  15

Gly Tyr Phe Thr
```

```
<210> SEQ ID NO 4
<211> LENGTH: 16
<212> TYPE: PRT
<213> ORGANISM: Dermatophagoides Farinae
<220> FEATURE:
<221> NAME/KEY: misc_feature
<222> LOCATION: (15)..(15)
<223> OTHER INFORMATION: Xaa can be any naturally occurring amino acid

<400> SEQUENCE: 4

Gln Gly Asp Tyr Val Glu Phe Asp Phe Val Val Gly Pro Ile Xaa Val
1               5                   10                  15

<210> SEQ ID NO 5
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: N=A+T+G+C
<220> FEATURE:
<221> NAME/KEY: misc_feature
<222> LOCATION: (5)..(5)
<223> OTHER INFORMATION: Y=C+T
<220> FEATURE:
<221> NAME/KEY: misc_feature
<222> LOCATION: (8)..(8)
<223> OTHER INFORMATION: Y=C+T
<220> FEATURE:
<221> NAME/KEY: misc_feature
<222> LOCATION: (11)..(11)
<223> OTHER INFORMATION: Y=C+T
<220> FEATURE:
<221> NAME/KEY: misc_feature
<222> LOCATION: (14)..(14)
<223> OTHER INFORMATION: Y=C+T
<220> FEATURE:
<221> NAME/KEY: misc_feature
<222> LOCATION: (17)..(17)
<223> OTHER INFORMATION: N=A+T+G+C
<220> FEATURE:
<221> NAME/KEY: misc_feature
<222> LOCATION: (20)..(20)
<223> OTHER INFORMATION: Y=C+T

<400> SEQUENCE: 5
cngaygaytt yttyccntay g                                             21

<210> SEQ ID NO 6
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: Y=C+T
<220> FEATURE:
<221> NAME/KEY: misc_feature
<222> LOCATION: (6)..(6)
<223> OTHER INFORMATION: R=A+G
<220> FEATURE:
<221> NAME/KEY: misc_feature
<222> LOCATION: (9)..(9)
<223> OTHER INFORMATION: Y=C+T
<220> FEATURE:
<221> NAME/KEY: misc_feature
<222> LOCATION: (12)..(12)
```

```
<223> OTHER INFORMATION: N=A+T+G+C
<220> FEATURE:
<221> NAME/KEY: misc_feature
<222> LOCATION: (15)..(15)
<223> OTHER INFORMATION: Y=C+T

<400> SEQUENCE: 6
gaygarcayg cntaytgga                                                        19

<210> SEQ ID NO 7
<211> LENGTH: 22
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: R=A+G
<220> FEATURE:
<221> NAME/KEY: misc_feature
<222> LOCATION: (6)..(6)
<223> OTHER INFORMATION: R=A+G
<220> FEATURE:
<221> NAME/KEY: misc_feature
<222> LOCATION: (9)..(9)
<223> OTHER INFORMATION: Y=C+T
<220> FEATURE:
<221> NAME/KEY: misc_feature
<222> LOCATION: (12)..(12)
<223> OTHER INFORMATION: N=A+T+G+C
<220> FEATURE:
<221> NAME/KEY: misc_feature
<222> LOCATION: (15)..(15)
<223> OTHER INFORMATION: R=A+G
<220> FEATURE:
<221> NAME/KEY: misc_feature
<222> LOCATION: (18)..(18)
<223> OTHER INFORMATION: R=A+G
<220> FEATURE:
<221> NAME/KEY: misc_feature
<222> LOCATION: (21)..(21)
<223> OTHER INFORMATION: N=A+T+G+C

<400> SEQUENCE: 7
aartcraayt cnacrtartc nc                                                    22

<210> SEQ ID NO 8
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: R=A+G
<220> FEATURE:
<221> NAME/KEY: misc_feature
<222> LOCATION: (4)..(4)
<223> OTHER INFORMATION: Y=C+T
<220> FEATURE:
<221> NAME/KEY: misc_feature
<222> LOCATION: (7)..(7)
<223> OTHER INFORMATION: N=A+T+G+C
<220> FEATURE:
<221> NAME/KEY: misc_feature
<222> LOCATION: (10)..(10)
<223> OTHER INFORMATION: R=A+G
<220> FEATURE:
<221> NAME/KEY: misc_feature
<222> LOCATION: (13)..(13)
<223> OTHER INFORMATION: R=A+G
<220> FEATURE:
<221> NAME/KEY: misc_feature
```

```
<222> LOCATION: (16)..(16)
<223> OTHER INFORMATION: N=A+T+G+C
<220> FEATURE:
<221> NAME/KEY: misc_feature
<222> LOCATION: (19)..(19)
<223> OTHER INFORMATION: Y=C+T

<400> SEQUENCE: 8
raaytcnacr tartcnccyt g                                              21

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 9
gttggtcata aaggacaacg                                                20

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 10
tcggtatcgt tcaagaagta                                                20

<210> SEQ ID NO 11
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: N=A+T+G+C
<220> FEATURE:
<221> NAME/KEY: misc_feature
<222> LOCATION: (6)..(6)
<223> OTHER INFORMATION: N=A+T+G+C
<220> FEATURE:
<221> NAME/KEY: misc_feature
<222> LOCATION: (9)..(9)
<223> OTHER INFORMATION: Y=C+T
<220> FEATURE:
<221> NAME/KEY: misc_feature
<222> LOCATION: (12)..(12)
<223> OTHER INFORMATION: N=A+T+G+C
<220> FEATURE:
<221> NAME/KEY: misc_feature
<222> LOCATION: (15)..(15)
<223> OTHER INFORMATION: Y=C+T
<220> FEATURE:
<221> NAME/KEY: misc_feature
<222> LOCATION: (18)..(18)
<223> OTHER INFORMATION: Y=C+T

<400> SEQUENCE: 11
gtnccncaya cncaygayg                                                 19

<210> SEQ ID NO 12
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
```

```
<221> NAME/KEY: misc_feature
<222> LOCATION: (1)..(1)
<223> OTHER INFORMATION: N=A+T+G+C
<220> FEATURE:
<221> NAME/KEY: misc_feature
<222> LOCATION: (4)..(4)
<223> OTHER INFORMATION: Y=C+T
<220> FEATURE:
<221> NAME/KEY: misc_feature
<222> LOCATION: (7)..(7)
<223> OTHER INFORMATION: Y=C+T
<220> FEATURE:
<221> NAME/KEY: misc_feature
<222> LOCATION: (10)..(10)
<223> OTHER INFORMATION: Y=C+T
<220> FEATURE:
<221> NAME/KEY: misc_feature
<222> LOCATION: (13)..(13)
<223> OTHER INFORMATION: N=A+T+G+C
<220> FEATURE:
<221> NAME/KEY: misc_feature
<222> LOCATION: (16)..(16)
<223> OTHER INFORMATION: N=A+T+G+C

<400> SEQUENCE: 12
ncaygaygay gtnggntgg                                               19

<210> SEQ ID NO 13
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 13
ttgtggccac acttttacgt ccag                                         24

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 14
ccattgcttc acgtaatctt                                              20

<210> SEQ ID NO 15
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 15
agccatttcc cgggaatgac caaatg                                       26
```

US 10,457,711 B2

DERMATOPHAGOIDES FARINAE PROTEIN

TECHNICAL FIELD

The present invention relates to a novel protein derived from Dermatophagoides farinae and utilization of the protein.

BACKGROUND ART

Typical examples of allergic diseases include allergic rhinitis such as pollinosis, allergic conjunctivitis, atopic type bronchial asthma and atopic dermatitis, and in recent years, the morbidity rates of these allergic diseases in Japan just keep increasing. It is known that a significant number of the causes of onset for atopic type bronchial asthma or atopic dermatitis involve house dust, which includes mite bodies, mite feces, fungi, hairs of animals such as pets. Particularly, it is known that allergens derived from house dust mites inhabiting houses play an important role (Non-Patent Literature 1).

Most of typical house dust mites inhabiting houses consist of Dermatophagoides Farinae (hereinafter, abbreviated to "Der f") and Dermatophagoides pteronyssinus (hereinafter, abbreviated to "Der p"). These house dust mites are known to propagate most effectively under warm and humid conditions; however, in present times with an increased number of highly airtight and highly heat-insulated buildings, there are more chances that the indoor environment can be maintained under conditions adequate for house dust mites all year round, and thus the population of house dust mites is still increasing. This is believed to be a factor causative of the increase in allergic diseases.

For the treatment of these allergic diseases, for example, an antihistamine drug, a steroidal antiinflammatory drug, an antileukotriene drug, a degranulation inhibitor, and a Th2 cytokine inhibitor are used; however, all of these are merely for symptomatic treatments. Meanwhile, allergen immunotherapy including subcutaneous allergen immunotherapy (SLIT) and sublingual allergen immunotherapy (SLIT) have been successively developed in recent years. Allergen immunotherapy is a method of treatment by which immune responses to an allergen are controlled by administering the allergen to the body in small amounts, and at the present moment, it is considered that allergen immunotherapy is the only method capable of complete cure of allergic diseases.

Development of allergen immunotherapy must be accompanied by research and understanding of causative allergens. For example, highly antigenic allergens called Der f 1, Der f 2, and Der f 3 have been reported to be found in the body or feces of Dermatophagoides farinae, which is said to have a large population in Japan, and these allergens have already been cloned (Non-Patent Literatures 2 and 3). According to the past reports, it is known that 80% or more of patients suffering from mite allergy have IgE specific to anyone or more of these allergens (Non-Patent Literature 4). In addition, exploratory research for Dermatophagoides farinae allergens is being actively conducted, and thus there is a demand for novel allergen proteins that are more useful for the prevention and treatment of allergic diseases caused by mite (Non-Patent Literature 5).

CITATION LIST

Non Patent Literature

Non-Patent Literature 1: Korsgaard J, et al., Allergy, 53:77-83, 1998

Non-Patent Literature 2: Dilworth R J, et al., Clinical and Experimental Allergy, 21:25-32, 1991

Non-Patent Literature 3 Yuuki T, et al. Jpn. J. Allegol., 39(6):557-561, 1990

Non-Patent Literature 4: Heymann P W, et al., J. Allergy Clin. Immunol., 83:1055-1067, 1989

Non-Patent Literature 5: Thomas W R, et al., Int. Arch. Allergy Immunol., 129:1-18, 2002

SUMMARY OF INVENTION

Technical Problem

The present invention relates to a novel Dermatophagoides farinae protein, and the provision of, for example, a diagnostic drug, a prophylactic drug, and a therapeutic drug for allergic diseases caused by Dermatophagoides farinae using the protein.

Solution to Problem

The inventors of the present invention conducted investigations in order to solve the problems described above, and the inventors succeeded in obtaining a new protein which is a molecular weight of approximately 110 kDa and exhibits high reactivity with serum IgE derived from patients of allergic diseases caused by Dermatophagoides farinae, from Dermatophagoides farinae feces, and found that this protein is useful as a diagnostic drug, a prophylactic drug, and a therapeutic drug for allergic diseases caused by Dermatophagoides farinae.

That is, the present invention relates to the following items 1) to 14).

1) A Dermatophagoides farinae protein selected from the group consisting of the following (a) to (c), or a fragment peptide thereof:
   (a) a protein including an amino acid sequence set forth in SEQ ID NO:2;
   (b) a protein including an amino acid sequence in which one or several amino acids have been substituted, deleted, or added relative to the amino acid sequence set forth in SEQ ID NO:2, and having allergenicity of Dermatophagoides farinae; and
   (c) a protein including an amino acid sequence having 90 or higher identity with the amino acid sequence set forth in SEQ ID NO:2, and having allergenicity of Dermatophagoides farinae.

2) A polynucleotide encoding a Dermatophagoides farinae protein selected from the group consisting of the following (a) to (c) or a fragment peptide thereof:
   (a) a protein including an amino acid sequence set forth in SEQ ID NO:2;
   (b) a protein including an amino acid sequence in which one or several amino acids have been substituted, deleted, or added relative to the amino acid sequence set forth in SEQ ID NO: 2, and having allergenicity of Dermatophagoides farinae; and
   (c) a protein including an amino acid sequence having 90% or higher identity with the amino acid sequence set forth in SEQ ID NO:2, and having allergenicity of Dermatophagoides farinae.

3) A polynucleotide selected from the group consisting of the following (d) to (f):
   (d) a polynucleotide including the base sequence set forth in SEQ ID NO:1;
   (e) a polynucleotide obtainable by hybridizing the base sequence set forth in SEQ ID NO: 1 and a polynucleotide including a complementary base sequence under stringent conditions, and capable of encoding a protein having allergenicity of Dermatophagoides farinae; and (f) a polynucleotide including a base sequence having 90% or higher identity with the base sequence set forth in SEQ ID NO:1, and capable of encoding a protein having allergenicity of Dermatophagoides farinae.

4) A prophylactic or therapeutic agent for an allergic disease caused by Dermatophagoides farinae, the prophylactic or therapeutic agent including the Dermatophagoides farinae protein according to 1) described above or a fragment peptide thereof as an active ingredient.

5) A diagnostic drug for an allergic disease caused by Dermatophagoides farinae, the diagnostic drug including the Dermatophagoides farinae protein according to 1) described above or a fragment peptide thereof as an active ingredient.

6) A binding protein binding to the Dermatophagoides farinae protein according to 1) described above or a fragment peptide thereof.

7) The binding protein according to 6) described above, wherein the binding protein is an antibody molecule.

8) The binding protein according to 6) described above, wherein the binding protein is a monoclonal antibody.

9) Use of the Dermatophagoides farinae protein according to 1) described above or a fragment peptide thereof, for the production of a prophylactic or therapeutic agent for an allergic disease caused by Dermatophagoides farinae.

10) Use of the Dermatophagoides farinae protein according to 1) described above or a fragment peptide thereof, for the production of a diagnostic drug for an allergic disease caused by Dermatophagoides farinae.

11) The Dermatophagoides farinae protein according to 1) described above or a fragment peptide thereof, for use in the prevention or treatment of an allergic disease caused by Dermatophagoides farinae.

12) The Dermatophagoides farinae protein according to 1) described above or a fragment peptide thereof, for use in the diagnosis of an allergic disease caused by Dermatophagoides farinae.

13) A method for preventing or treating an allergic disease caused by Dermatophagoides farinae, the method including administering the Dermatophagoides farinae protein according to 1) described above or a fragment peptide thereof to a patient.

14) A method for diagnosing an allergic disease caused by Dermatophagoides farinae, the method including administering the Dermatophagoides farinae protein according to 1) described above or a fragment peptide thereof to a test subject.

Advantageous Effects of Invention

The Dermatophagoides farinae protein of the present invention exhibits high reactivity with serum IgE derived from a patient of an allergic disease caused by Dermatophagoides farinae, and therefore, the protein can be utilized for the diagnosis, prevention, and treatment of allergic diseases caused by Dermatophagoides farinae. Since this Dermatophagoides farinae protein is a different protein from known Dermatophagoides farinae allergens, particularly Der f 1 (molecular weight about 27 kDa), Der f 2 (molecular weight about 15 kDa), and Der f 3 (molecular weight about 29 kDa), a more useful allergen immunotherapy is enabled by combining this protein with these allergens.

DESCRIPTION OF EMBODIMENTS

Dermatophagoides Farinae Protein

Figure 1:
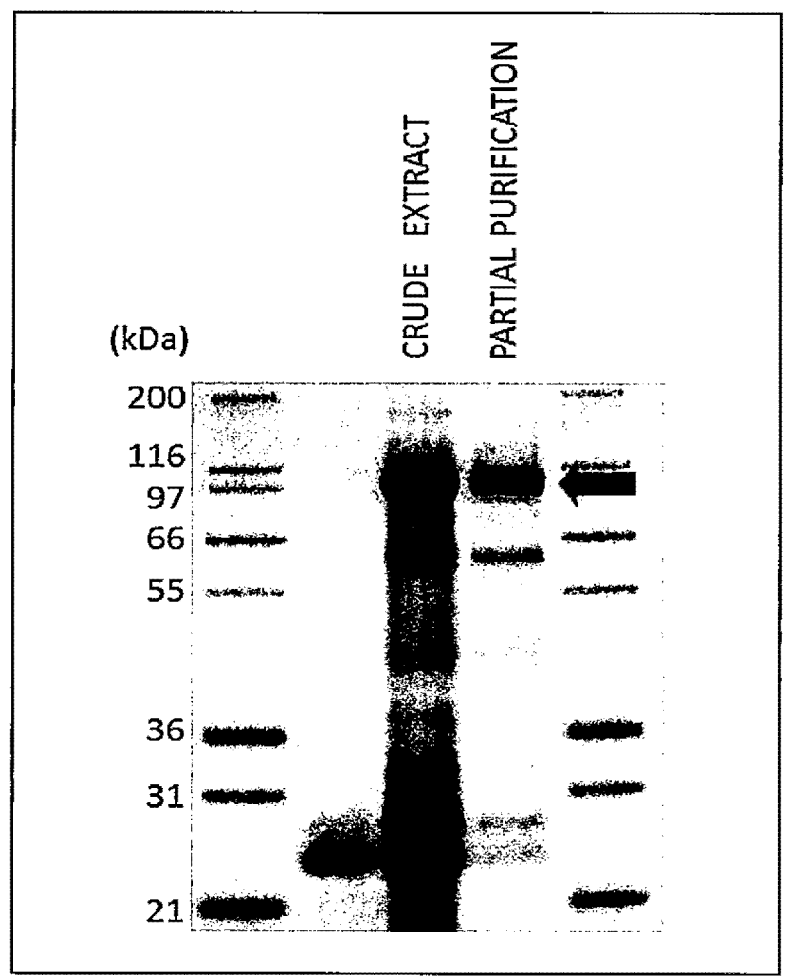
FIG. 1 is a diagram illustrating the results of analyzing a crude extract and a partial purification product (fractionated by anion exchange chromatography using FPLC) of Dermatophagoides farinae by SDS-polyacrylamide gel electrophoresis (SDS-PAGE).

The Dermatophagoides farinae protein of the present invention is a protein selected from the group consisting of the following (a) to (c), or a fragment peptide thereof:

(a) a protein including an amino acid sequence set forth in SEQ ID NO:2;

(b) a protein including an amino acid sequence in which one or several amino acids have been substituted, deleted, or added relative to the amino acid sequence set forth in SEQ ID NO:2, and having allergenicity of Dermatophagoides farinae; and (c) a protein including an amino acid sequence having 90% or higher identity with the amino acid sequence set forth in SEQ ID NO:2, and having allergenicity of Dermatophagoides farinae.

The protein of (a) including the amino acid sequence set forth in SEQ ID NO:2 is a protein that has been separated and purified from Dermatophagoides farinae by performing fractionation by anion exchange chromatography using FPLC, and then removing proteins having molecular weights of 100 kDa or less by an ultrafiltration method. This protein has the following properties.

i) The protein exhibits a binding reaction with serum IgE from a patient of an allergic disease caused by Dermatophagoides farinae.

ii) The protein activates basophils in a patient of an allergic disease caused by Dermatophagoides farinae.

iii) The protein has a molecular weight of about 110 kDa as measured by SDS-polyacrylamide gel electrophoresis (SDS-PAGE).

Therefore, this protein is a novel Dermatophagoides farinae protein that is different from known Dermatophagoides farinae allergens including Der f 1 (molecular weight about 27 kDa), Der f 2 (molecular weight about 15 kDa), and Der f 3 (molecular weight about 29 kDa) (Non-Patent Literature 5).

The Dermatophagoides farinae protein of the present invention includes a protein including an amino acid sequence in which one or several amino acids have been substituted, deleted or added relative to the amino acid sequence set forth in SEQ ID NO:2 (item (b) described above), as long as the protein has allergenicity of Dermatophagoides farinae. The Dermatophagoides farinae protein including such an amino acid sequence may be, for example, an isoform of a Dermatophagoides farinae protein including the amino acid sequence set forth in SEQ ID NO:2. Here, several amino acids that are deleted, substituted or added indicate, for example, 1 to 10 amino acids, and more preferably 1 to 5 amino acids. The addition as described above includes addition of one to several amino acids to both terminals.

In the present specification, an "allergen" refers to a causative substance inducing an allergic disease. The "allergenicity of Dermatophagoides farinae" includes activity of binding with IgE on mast cells and inducing an immediate type allergic reaction in an atopic person (De Weck, AL, et al., Int. Arch. Allergy Immunol., 146:177-189, 2008), as well as activity of simply binding with IgE in the serum (see Example 2 (i)).

The Dermatophagoides farinae protein of the present invention includes a protein including a protein having 90% or higher identity with the amino acid sequence set forth in SEQ ID NO:2 when amino acid sequences corresponding to the amino acid sequence set forth in SEQ ID NO:2 are appropriately aligned (item (c) described above), as long as the protein has allergenicity of Dermatophagoides farinae.

Here, identity with the amino acid sequence set forth in SEQ ID NO:2 is preferably 95% or higher, and more preferably 98% or higher. In regard to the identity with an amino acid sequence, for example, a method of performing calculation by using BLAST (Basic Local Alignment Search Tool at the National Center for Biological Information) and setting the option parameters to initial set values, can be applied.

The Dermatophagoides farinae protein of the present invention may be a portion of a larger protein such as a fusion protein. Here, the sequence to be added to the fusion protein may be, for example, a sequence that is useful for purification, such as multiple histidine residues; or an addition sequence for securing stability at the time of recombinant production.

The Dermatophagoides farinae protein of the present invention may also be a fragment peptide having only a region essential for allergenenicity. For example, in particular, a partial fragment including an epitope (T-cell epitope) that is specifically recognized by T-cells from patients of allergic diseases caused by Dermatophagoides farinae may be suitably mentioned. It is considered that the length of the peptide that binds with an HLA Class II molecule and then is presented as an antigen, includes approximately 10 to 34 amino acid residues based on the results of a peptide analysis (Chicz, R. M, et al., J. Exp. Med., 178:27-47, 1993), and therefore, a fragment including at least one T-cell epitope also includes a peptide having such a length.

T-cell epitopes can be identified by an examination using overlapping peptides including about 10-mers to 20-mers, for example, the method described in Jahn-Schmid B. J., et al., Allergy Clin Immunol. 126(5):1068-71, 2010, or in Sone, T, et al., J. Immunol., 161:448-457, 1998.

Polynucleotide Encoding Dermatophagoides Farinae Protein

The polynucleotide of the present invention is a polynucleotide encoding the Dermatophagoides farinae protein or a fragment peptide thereof, and suitable examples thereof include: (d) a polynucleotide including the base sequence set forth in SEQ ID NO:1; (e) a polynucleotide that is obtained by hybridizing the base sequence set forth in SEQ ID NO:1 and a polynucleotide including a complementary base sequence under stringent conditions, and encodes a protein having allergenicity of Dermatophagoides farinae; and (f) a polynucleotide that includes a base sequence having 90% or higher identity with the base sequence set forth in SEQ ID NO:1, and encodes a protein having allergenicity of Dermatophagoides farinae.

The polynucleotides of (e) and (f) include variants of the polynucleotide of (d). These variants include naturally occurring allelic variants, and non-naturally occurring variants that can be produced using mutagenic techniques that are well known in the pertinent field.

The polynucleotides of the present invention include not only double-stranded DNAs but also various single-stranded DNAs or RNAs called sense strands and antisense strands that constitute the double-stranded DNAs. An antisense strand can be utilized as, for example, a probe. DNAs include, for example, cDNAs and genomic DNAs obtainable by cloning, chemical synthesis technologies, or combinations thereof. The polynucleotides according to the invention may also include base sequences such as sequences in untranslated regions (UTR) and vector sequences (including expression vector sequences), in addition to base sequences encoding the polypeptides according to the invention.

Here, stringent conditions may be, for example, the conditions described in Molecular Cloning: A Laboratory Manual (Second Edition, J. Sambrook et al., 1989). Namely, the stringent conditions may be conditions in which a polynucleotide is kept at a constant temperature of 65° C. for 8 to 16 hours together with a probe in a solution containing 6× SSC (composition of 1× SSC: 0.15 M sodium chloride, 0.015 M sodium citrate, pH 7.0), 0.5% SDS, 5× Denhardt, and 100 mg/mL herring sperm DNA, and is subjected to hybridization.

The identity with the base sequence set forth in SEQ ID NO:1 is preferably 95% or higher, and more preferably 98% or higher. In regard to the identitywith the relevant base sequence, for example, a method of performing calculation by using BLAST and setting the option parameters to the initial set values, can be applied.

Acquisition of Polynucleotide Encoding Dermatophagoides Farinae Protein

A polynucleotide encoding the Dermatophagoides farinae protein of the present invention can be cloned from Dermatophagoides farinae, and examples of the cloning method include methods of performing cloning using existing means, for example, a shot gun method and a PCR method.

For example, it is desirable that probes which are specifically hybridized with a part of the base sequence of the polynucleotide of the present invention, and screening of a genomic DNA library or a cDNA library be performed using the probe. Regarding such a probe, a probe having any sequence or any length may be used, as long as the probe is a probe which specifically hybridizes with at least a portion of the polynucleotide according to the present invention or a complementary strand thereof.

The polynucleotide of the present invention can also be obtained by acquiring a sequence that hybridizes with a polynucleotide including a portion or the entirety of the polynucleotide of the present invention, using an appropriate principle. For example, a PCR method of performing hybridization using a polynucleotide including a portion of the polynucleotide of the present invention as a primer, and a method of using the aforementioned polynucleotide including a portion of the polynucleotide of the present invention as a probe, may be employed.

For example, in a method of using amplification means such as PCR, primers are respectively produced from the sequences of the 5'-side and the 3'-side of the polynucleotide of the present invention (or complementary sequences), an amplification reaction such as PCR is performed using these primers and using a genomic DNA (or a cDNA) as a template so as to amplify the DNA region that is inserted between the two primers, and thereby a DNA fragment including the polynucleotide can be acquired in a large quantity.

The polynucleotide provided by the present invention can also be produced by, for example, modifying a polynucleotide including the base sequence set forth in SEQ ID NO:1 by a method such as a deliberate or random mutation-introducing method.

Here, planning for mutation at the time of systematically introducing a mutation can be carried out by, for example, considering a characteristic sequence on the polynucleotide sequence. Examples of a method for randomly introducing a mutation include a PCR method and a method based on a mutagenic treatment. A method for systematically introducing a mutation may be a site-directed mutagenesis method, and specifically, the method can be carried out using, for example, a Site-Directed Mutagenesis SystemMutan-Super Express Kmkit (Takara Bio, Inc.). A recombinant PCR method (PCR protocols, Academic Press, New York, 1990) can also be used.

Production of Dermatophagoides Farinae Protein

The Dermatophagoides farinae protein of the present invention can be obtained through separation and purification from Dermatophagoides farinae. The method for separation and purification is not particularly limited; however, for example, it is desirable to subject a Dermatophagoides farinae extract to separation and purification using conventionally known techniques such as gel filtration, ion exchange chromatography, and affinity chromatography.

The Dermatophagoides farinae protein can be collected by introducing a recombinant vector produced by incorporating the polynucleotide of the present invention into an appropriate vector, into host cells, and thereby expressing the Dermatophagoides farinae protein intracellularly or extracellularly.

The vector for inserting the polynucleotide of the present invention is not particularly limited as long as the vector is capable of replication in hosts such as bacteria such as *Escherichia coli* and *Bacillus subtilis*, yeasts, or animal cells. Examples of the vector include a plasmid DNA and a phage DNA. Regarding the vector DNA used for construction of an expression vector, a vector DNA that is easily available and widely distributed is used. Examples thereof include pUC19 (Takara Bio, Inc.), pTV118N (Takara Bio, Inc.), pMAMneo (Clontech Laboratories, Inc.), pGEX (GE Health care Corp.), pET160 (Invitrogen, Inc.), and pDEST (Invitrogen, Inc.).

In order to transform a host using the recombinant vector, the transformation can be carried out using, for example, a protoplast method, a competent cell method, or an electroporation method. The host is not particularly limited, and any host can be used. For example, an animal, animal-derived cells, a plant, plant-derived cells, and microorganisms can be used.

A transformant thus obtained may be cultured under appropriate conditions using a medium containing, for example, a carbon source that can be assimilated, a nitrogen source, a metal salt, and vitamins. Proteins are collected and purified by general methods from the medium thus obtained, and the Dermatophagoides farinae protein of the present invention can be obtained.

Prevention or Treatment of Allergic Diseases caused by Dermatophagoides Farinae

Since the Dermatophagoides farinae protein of the present invention or a fragment peptide thereof exhibits high reactivity with serum IgE derived from patients of allergic diseases caused by Dermatophagoides farinae, the protein or the fragment peptide can serve as a prophylactic or a therapeutic agent for allergic diseases caused by Dermatophagoides farinae, and can be used for the prevention or treatment of allergic diseases caused by Dermatophagoides farinae when administered to the patients.

Here, prevention or treatment of allergic diseases caused by Dermatophagoides farinae specifically refers to the prevention or treatment for all allergic diseases caused by specific antigens of Dermatophagoides farinae, and examples of the allergic diseases include atopic type bronchial asthma, allergic rhinitis, allergic conjunctivitis, and atopic dermatitis.

Prevention or treatment of the allergic diseases caused by Dermatophagoides farinae may be, for example, allergen immunotherapy for allergic diseases caused by Dermatophagoides farinae.

Since the Dermatophagoides farinae protein of the present invention is different from the conventionally known allergens including Der f 1 and Der f 2, when the protein is combined with these, more useful allergen immunotherapy can be achieved.

When the prophylactic or therapeutic agent of the present invention for allergic diseases caused by Dermatophagoides farinae is used as an allergen immunotherapeutic agent, the Dermatophagoides farinae protein or a fragment peptide thereof is used directly or in a powder form after being dried, or it is preferable that the prophylactic or therapeutic agent be produced as a mixed preparation in which various additives that are generally used, for example, a stabilizer, an excipient, a dissolution aid, an emulsifying suspending agent, a buffer gent, a soothing agent, a preservative, and a colorant have been added by conventional methods as necessary.

For example, a Dermatophagoides farinae protein that has been purified into a powder form is dissolved in physiological saline containing phenol added thereto, and this solution can be used as a stock solution of an antigen for allergen immunotherapy.

When the prophylactic or therapeutic agent of the present invention for allergic diseases caused by Dermatophagoides farinae is used as an allergen immunotherapeutic agent, the prophylactic or therapeutic agent can include an adjuvant having immunopotentiative action on the occasion of administration. Examples of the adjuvant include Complete Freund's adjuvant (CFA), Incomplete Freund's adjuvant (IFA) aluminum potassium sulfate, Lipid A, monophosphoryl lipid A; a bacterial formulation such as BCG (Bacillus-Calmette-Guerrin); a nucleic acid such as CpG-DNA or dsRNA; a bacterial component preparation such as tuberculin; a natural polymer material such as keyhole limpet hemocyanin or yeast mannan; muramyl tripeptide and muramyl tripeptide or a derivative thereof; alum, a nonionic block copolymer; and a cytokine such as interleukin 2 (IL-2), granulocyte macrophage colony stimulating factor (GM-CSF), interferon-α(IFN-α), or interferon-β (IFN-β). One kind or a combination of two or more kinds thereof can be used. The adjuvant maybe used by simultaneously administration together with the Dermatophagoides farinae protein of the present invention or a fragment peptide thereof, in a mixed state or as an emulsion.

The prophylactic or therapeutic agent of the present invention for allergic diseases caused by Dermatophagoides farinae can be administered by an administration method involving a conventional route of administration, for example, percutaneous, transmucosal, peroral, intradermal, subcutaneous, intramuscular, interperitoneal, or nasal instillation administration. The prophylactic or therapeutic agent can be produced as formulations of various dosage forms such as a tablet, a capsule, a granular preparation, a powder preparation, a troche, a sublingual tablet, a syrup, an injectable preparation, a suppository, an inhalant, a percutaneously absorbable preparation, an eye drop, a nasal drop, an intranasal spray, a poultice, a PAP preparation, an ointment, a lotion, and a cream, according to the form of administration.

The dose and the frequency of administration for the prophylactic or therapeutic agent of the present invention for allergic diseases caused by Dermatophagoides farinae may vary depending on, for example, the route of administration and symptoms; however, for example, the amount of administration can be appropriately selected to be in the range of about 0.1 to 100 mg per dose, and the prophylactic or therapeutic agent can be administered once to several times per week.

Diagnosis of Allergic Diseases Caused by Dermatophagoides Farinae

The Dermatophagoides farinae protein of the present invention or a fragment peptide thereof can serve as a diagnostic drug for allergic diseases caused by Dermatophagoides farinae, specifically an intradermal reaction diagnostic drug for allergic diseases caused by Dermatophagoides farinae. By intradermally injection with a small amount of the protein or the fragment peptide to a test subject, the allergic state or immune state of a living body against Dermatophagoides farinae can be understood, and this can be used for confirmation of an antigen or diagnosis of a disease.

When the protein or a fragment peptide thereof is used as an intradermal reaction diagnosis reagent, the Dermatophagoides farinae protein of the present invention or a fragment peptide thereof obtained by the present method as described above is used after, for example, drying into a powder form, dissolving this in physiological saline containing phenol, and diluting the solution.

Binding Protein Capable of Binding to Dermatophagoides Farinae Protein or Fragment Peptide Thereof A binding protein that binds to the Dermatophagoides farinae protein of the present invention or a fragment peptide thereof is a protein that can specifically bind to the Dermatophagoides farinae protein of the present invention or a fragment peptide thereof. Examples of the binding protein include antibody molecules such as immunoglobulins (for example, IgA, IgD, IgG, IgM, and IgY), Fab fragment, F(ab')2 fragment, a single-stranded antibody fragment (scFv), and a single domain antibody (Carter, P J, Nat. Rev. Immunol., 6:343-357, 2006); and antibody-like molecules such as Affibody, DARPins, and Avimer. Examples of the antibody molecules include polyclonal antibodies, and monoclonal antibodies (for example, a mouse antibody, a chimeric antibody, a humanized antibody, or a human antibody); however, the antibody molecules are not limited to these.

The binding protein can be produced using various known methods, and the production method is not particularly limited.

The binding protein can be utilized for, for example, the identification of an organism expressing the Dermatophagoides farinae of the present invention, a tissue or cells thereof. For example, the binding protein can be utilized in order to measure the presence or absence of a Dermatophagoides farinae protein in the atmosphere, in an indoor space, or in human mucus. The measurement can be carried out by a known immunological method, and for example, the measurement can be carried out by ELISA.

The binding protein can also be used for the treatment of allergic diseases caused by Dermatophagoides farinae.

Hereinafter, the present invention will be specifically described by way of Examples. However, the present invention is not limited to these Examples.

EXAMPLES

Example 1

Purification of Protein from Dermatophagoides Farinae

A medium in which mites had been bred for a long time period was dried under humidification, and the dried medium was passed through a sieve of mesh size 180 μm and then was suspended in phosphate buffered saline (PBS). The suspension was immediately passed through a sieve of mesh size 53 μm, and insoluble components were removed. The PBS suspension of feces therein was left to stand at 37° C. for 2 hours, and soluble components were extracted. The extract was centrifuged at 5,000 rpm at 4° C. for 30 minutes, and the supernatant was dialyzed for 2 days using a dialysis membrane of a fractionation molecular weight of 12,000 to 14,000. Thus, low molecular weight components were removed. The dialyzed supernatant was concentrated using a centrifugal concentrator (VIVASPIN 20, MWCO 10 kDa), and a crude extract was obtained.

10 volumes of 20 mM Tris-HCl (pH 9.0) were added to the crude extract, and then the mixture was applied to a cation column (VIVAPURE S Maxi M) and was centrifuged (500 g, 5 minutes). Subsequently, an elution fraction was collected. The elution fraction was applied to anion chromatography (UNO Q 1 mL, Bio-Rad Laboratories, Inc.), and was eluted with a NaCl gradient of 0 to 1 M. Fractions containing a target protein were collected, and low molecular weight fractions were removed using a centrifugal concentrator (VIVASPIN 6, MWCO 100 kDa). Thus, a purified protein was obtained. The results of analyzing the purified protein by SDS-polyacrylamide gel electrophoresis (SDS-PAGE) are shown in FIG. 1.

Example 2

Figure 2:
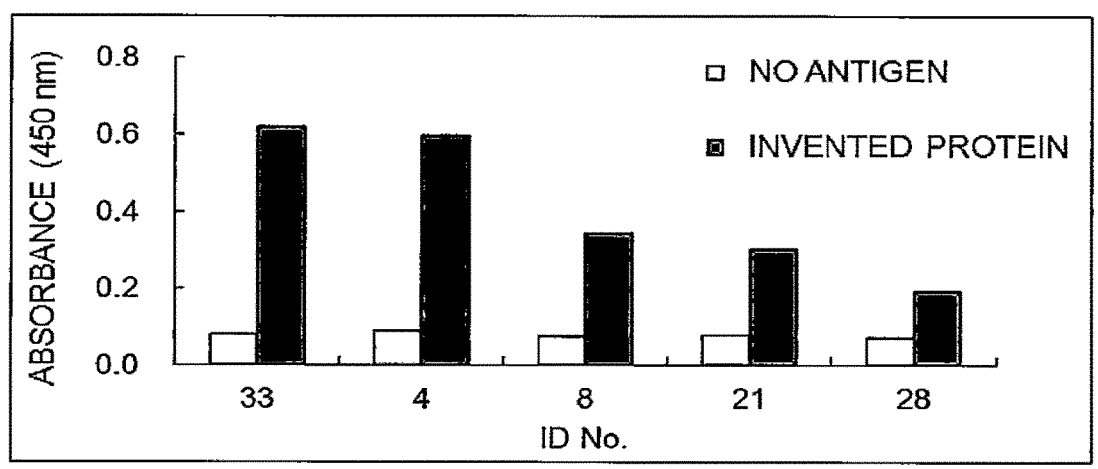
FIG. 2 is a diagram illustrating the results of an analysis of the purified allergen-specific IgE antibody titer using the sera from five patients (RAST Score ≥2) which have allergic diseases caused by Dermatophagoides farinae.

Confirmation of Allergenicity of Purified Antigen (i) Confirmation of reactivity with serum IgE from patient of allergic disease caused by Dermatophagoides farinae A 20 μg/mL solution of the protein of the present invention or a known mite antigen (Der f 1) was prepared, and the solution was added to a MAXISORP 96-well plate (Nunc A/S) in an amount of 1 μg/50 μL/well. Subsequently, the plate was left to stand overnight at 4° C., and thereby the antigen was immobilized. The next day, the plate was washed, and then a 1% bovine serum albumin-containing PBS was added. The plate was left to stand at room temperature for one hour, and thereby blocking was performed. The plate washing, subsequently a patient serum that had been diluted five times was added to the plate, and the plate was left to stand at room temperature for 2 hours. As a negative control, a commercially available human AB serum (CELLECT (R) Human AB serum; MP Biomedicals, LLC) was used. After the plate washing, a secondary antibody (HRP-labeled goat anti-human IgE antibody, Novus Biologicals, LLC) diluted 7000 times with a 1% bovine serum albumin-containing PBS was added, and the plate was left to stand at room temperature for 40 minutes. After the plate washing, TMB color development was performed using a TMB substrate reagent set (BD Biosciences Co.) by leaving the plate to stand at room temperature in the dark. Then color development was stopped by adding 1 N sulfuric acid to the plate, and the absorbance at a wavelength of 450 nm was measured using a microplate reader. The results are shown in FIG. 2.

Figure 3:
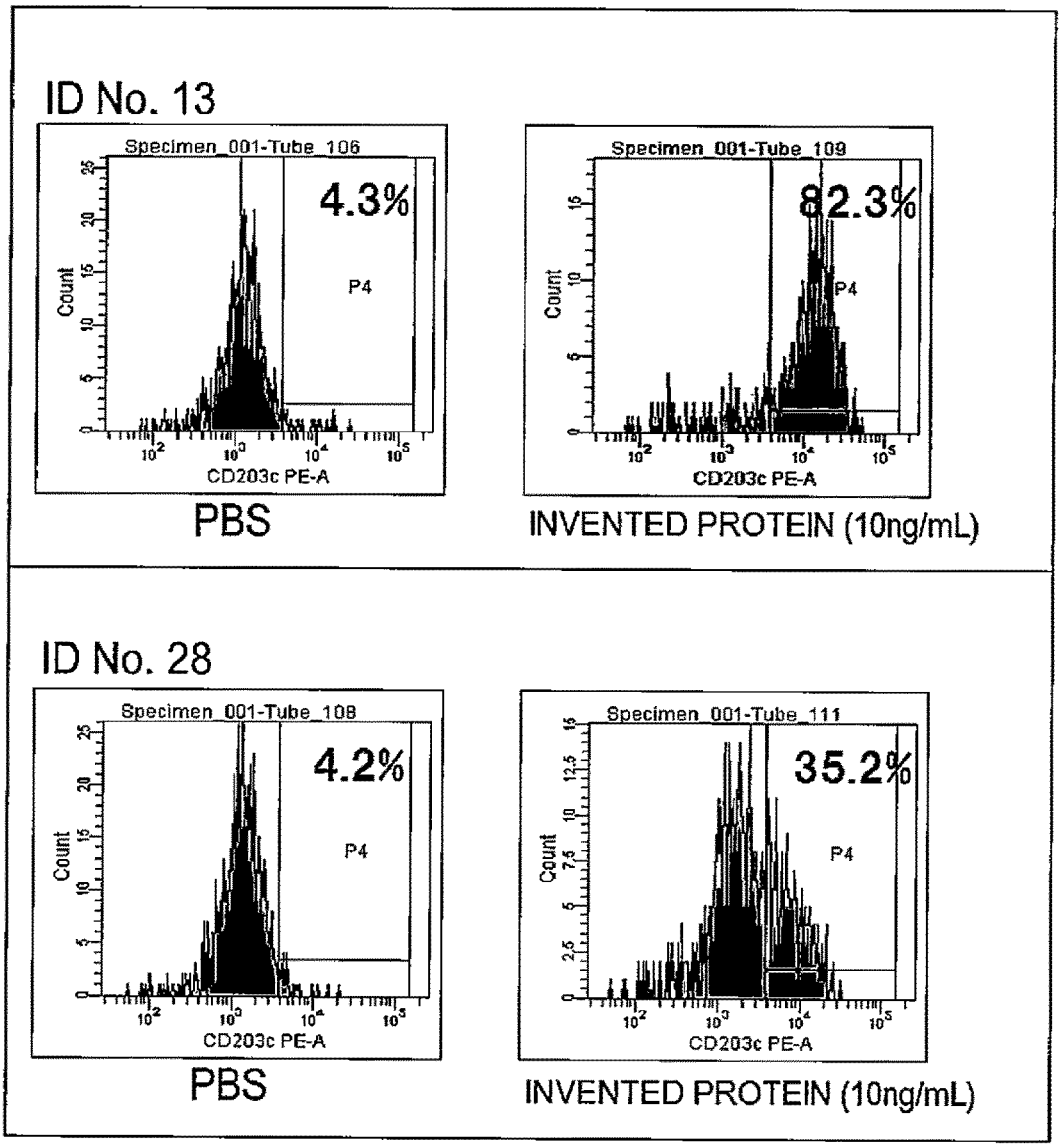
FIG. 3 is a diagram illustrating the results of an evaluation regarding the allergenicity (upregulation of CD203c on basophils) using peripheral blood of patients (two persons) of allergic diseases caused by Dermatophagoides farinae. Percentage in the diagram represents the population of P4 gate in the cells as objects of analysis.

(ii) Activation of basophils of patient of allergic disease caused by Dermatophagoides farinae It is known that, the expression of CD203c is increased in basophils that stimulated by allergens (De Weck, AL, et al., Int. Arch. Allergy Immunol., 146:177-189, 2008). Based on this principle, activations of basophils inpatient blood was analyzed by using an allergenicity kit (Beckman Coulter, Inc.). 20 µL of a solution of the protein allergen of the present invention (final concentration: 1 to 100 ng/ml) and 20 µL of an antibody cocktail containing CD3-PC7, CRTH2-FITC and CD203c-PE were added to 100 µL of heparinized whole blood, and the mixture was incubated at 37° C. for 15 minutes. 100 µL of a stop solution and 2 mL of a fix and lyse solution were added, and the mixture was allowed to react at room temperature for 10 minutes. After the mixture was centrifuged (200 ×g, 5 minutes), the supernatant was removed, and 3 mL of a phosphate buffer solution (PBS) was added to the cells. The mixture was centrifuged again. After the supernatant was removed, the cells were suspended in a 0.1% formaldehyde-containing PBS, and the suspension was analyzed using a flow cytometer (FACSCanto, BD Biosciences Co.). Based on the acquired data, basophils within blood cells were analyzed by utilizing that CD3-PC7 expression was negative while CRTH2-FITC expression was positive as a selection marker, and the expression intensity of CD203c was evaluated. The results are shown in FIG. 3. The expression of CD203c on the basophils treated with allergen was higher than the expression on the basophils treated with PBS only.

Example 3

Determination of Base Sequence and Amino Acid Sequence

<Determination of partial internal amino acid sequence>

In order to clearly define the partial amino acid sequence in the protein of the present invention, an analysis of fragments obtainable by limited proteolysis using a protease was performed. 50 µg of the purified protein was subjected to SDS-PAGE, and then the gel near the band of the molecular weight of 110 kDa was shredded. Subsequently, the shredded gel was stirred and washed (20 minutes ×2 times) in 1 mL of purified water. After the additions of 300 µL of 7 mol/L guanidine/0.5 mol/L Tris-HC1/0.01 mol/L EDTA (pH 8.5) and 10 µL of 2-mercaptoethanol, the mixture was subjected to nitrogen purge and an ultrasonic treatment and then was left to stand at room temperature for 2 hours, and thereby the mixture was reduced. Next, 10 µL of 4-vinylpyridine was added, and the mixture was subjected to nitrogen purge and an ultrasonic treatment (1 minute) Subsequently, the mixture was left to stand at room temperature for 30 minutes, and thereby alkylation was performed. The reaction solution was discarded, subsequently 1 mL of 0.1 vol % trifluoroacetic acid was further added to the gel, and it was checked that the gel was acidic. Subsequently, the mixture was stirred for one hour. The solution was discarded, and the gel was stirred (20 minutes ×2 times) in 1 mL of 0.025 mol/L ammonium hydrogen carbonate/50 vol % acetonitrile. The solution was discarded, and the gel was stirred in 1 mL of acetonitrile for 5 minutes. Subsequently, the solution was discarded, and the gel was dried under reduced pressure in a centrifugal evaporator. Lysyl endopeptidase dissolved in a 0.025 mol/L ammonium hydrogen carbonate solution was added to the gel at an enzyme/substrate ratio of 1/20, and the mixture was left to stand on ice so as to cause the gel to swell for one hour. A 0.025 mol/L ammonium hydrogen carbonate solution was added, the solution was completely penetrated into the gel, and then the gel was allowed to react at 37° C. for 17 hours. The reaction solution was collected (Solution [1]. In order to extract peptides, 100 µL of 0.1 vol % trifluoroacetic acid/50 vol % acetonitrile was added to the remaining gel, the mixture was stirred for 20 minutes, and then an extract solution was collected (Solution [2]). The gel was further stirred in 100 µL of acetonitrile for 20 minutes, and then an extract solution was collected (Solution [3]). The solution [1] to [3] were mixed, the mixture was concentrated under reduced pressure, and then the concentrate was applied to reverse phase high performance liquid chromatography (XBRIDGE C18) and was subjected elution and fractionation at a gradient of 0 to 80 wt % of acetonitrile. Two maj or peptides were collected, and N-terminal amino acid sequences were analysed using a protein sequencer (PROCISE 492cLC; Applied Biosystems, Inc.). As a result,
Thr-Asp-Asp-Phe-Phe-Pro-Tyr-Ala-Ser-Asp-Glu-His-Ala-Tyr-Trp-Thr-Gly-Tyr-Phe-Thr [partial amino acid sequence 1 (SEQ ID NO:3)] and
Gln-Gly-Asp-Tyr-Val-Glu-Phe-Asp-Phe-Val-Val-Gly-Pro-Ile-X-V al [partial amino acid sequence 2 (SEQ ID NO:4) ] were obtained.

<Extraction of Dermatophagoides farinae RNA>

RNA was extracted from Dermatophagoides farinae that had been frozen in liquid nitrogen, by the following procedure using a RNeasy Mini kit (Qiagen N.V.). 600 µL of Buffer RLT was added to 10 mg of Dermatophagoides farinae, and the mites were homogenized by passing through an 18 G injection needle. The Dermatophagoides farinae suspension was added to a QIA shredder spin column (Qiagen N.V.) and was centrifuged (15,000 rpm, 2 minutes), and a flow-through was collected. 600 µL of a 70% ethanol aqueous solution was added to the collected RNA solution, and then the mixture was added to a RNeasy Mini column and was centrifuged (10,000 rpm, 15 seconds). The column was further washed with 350 µL of Buffer RW1, and then a DNase treatment was performed using an RNase-Free DNase set (Qiagen N.V.). The column was washed with 350 µL of Buffer RW1, and then purification of RNA was performed according to the protocol of the RNeasy Mini Kit. After purification, 30 µL of RNase Free $H_2O$ was added, and thus total RNA was collected.

<Production of Dermatophagoides farinae cDNA> cDNA was synthesized from the total RNA thus obtained, using a Superscript III First-Strand Synthesis System for RT-PCR (Invitrogen, Inc.). 3 µg of the total RNA was suspended in 8 µL of purified water, 1 µL of oligo (dT) 20 and 1 µl, of 10 mM dNTP were added, and then the mixture was incubated at 65° C. for 5 minutes. The mixture was cooled on ice for 2 minutes, and then 2 µL of 10× RT buffer, 1 µL of 25 mM $MgCl_2$, 2 µL of 0.1 M DTT, 1 µL of RNaseOUT (40U/µl), and 1 µL of Superscript III Reverse Transcriptase were added. The mixture was thoroughly mixed. The mixture was incubated at 50° C. for 50 minutes, and then the mixture was treated at 85° C. for 5 minutes to terminate the reaction.

<Determination of cDNA Sequence>

Degenerate primers were designed from the partial amino acid sequences 3 and 4. Primer 1 as a sense primer corresponding to the partial amino acid sequence 3, and Primer 2 as a downstream primer were designed. Similarly, Primer 3 as an antisense primer corresponding to the partial amino acid sequence 4, and Primer 4 as an upstream primer were designed. The mite cDNA as template was subjected to nested PCR using KOD FX Neo (Toyobo Co., Ltd.) and these primers. The PCR product electrophoresed in 2% agarose gel (Nacalai Tesque, Inc.), and then a gel slice containing amplified band were purified with a Wizard SV Gel and PCR Clean-Up System (Promega Corp.). Using Primer 2 and Primer 4 as primers, the purified PCR product was subjected to PCR with KOD Fx neo, and then the PCR product was purified with a Wizard SV Gel and PCR Clean-Up System (Promega Corp.). After purification, the DNA sequence was analyzed using a BigDye Xterminator Kit (Applied Biosystems, Inc.) and a DNA sequencer (3130×1; Applied Biosystems, Inc.), and thus intermediate sequence were obtained.

Next, for an analysis of the 3'-terminal sequence, a Dermatophagoides farinae cDNA containing an anchor sequence at the 3'-end was synthesized using a 5'/3' RACE kit 2nd generation (Roche Holding AG). Nested PCR with KOD Fx neo was performed using two nested primers, namely, Primer 5 and Primer 6 designed based on the sequences obtained from the intermediate sequence. The DNA sequence of the PCR product thus obtained was analyzed, and thus the 3'-terminal sequence was obtained.

A partial sequence of 1850 bp was obtained by an analysis of the intermediate sequence and the 3'-terminal sequence. Proteins having homology with these partial sequences were retrieved from the NCBI database, and the partial sequence had 37% homology with hypothetical protein CAPTEDRAFT_151096 (GenBank: ELT89240.1) of Capitella teleta, 40% homology with hypothetical protein LOTGIDRAFT_207233 (GenBank:ESO84761.1)with Lottia gigantean, and 47% homology with PREDICTED: lysosomal alpha-mannosidase-like (NCBI Reference Sequence: XP_003383866.1) of Amphimedon queenslandica. Thus, homologous sequences between ELT89240.1, ESO84761.1, and XP_003383866.1 were analyzed, and degenerate primers Primer 7 and Primer 8 were designed according to the identical sequences of amino acids in the vicinity of the N-terminal. Primer 9 and Primer 10 were designed from the intermediate sequence. Primer 9, Primer 10, Primer 7 and Primer 8 were used for nested PCR with KOD Fx neo and Dermatophagoides farinae cDNA. The DNA sequence of the amplified PCR product was analyzed, and a partial sequence of the 5'-terminal was obtained.

In order to analyze the 5'-terminal sequence, a 5' RACE was performed using a SMARTer RACE cDNA Amplification Kit (Clontech Laboratories, Inc.). Dermatophagoides farinae total RNA was purified using a NucleoTrap mRNA mini (MACHEREY-NAGEL GmbH & Co. KG) to obtain purified Dermatophagoides farinae polyA mRNA. cDNA containing the adaptor sequence at the 5'-end was synthesized from the purified polyA mRNA using a SMARTer RACE cDNA Amplification Kit.

This cDNA was subjected to touchdown PCR using Primer 11 designed from the 5'-terminal partial sequence and PrimeStar HS DNA polymerase (Takara Bio, Inc.). Regarding the reaction conditions, the protocol of the SMARTer RACE cDNA Amplification Kit was followed. The DNA sequence of the PCR product thus obtained was analyzed, and the sequence up to the 5'-end was obtained.

TABLE 1

Primers used

| | |
|---|---|
| Primer 1 | 5'-CNG AYG AYT TYT TYC CNT AYG-3'<br>SEQ ID NO: 5 |
| Primer 2 | 5'-GAY GAR CAY GCN TAY TGG A-3'<br>SEQ ID NO: 6 |
| Primer 3 | 5'-AAR TCR AAY TCN ACR TAR TCN C-3'<br>SEQ ID NO: 7 |
| Primer 4 | 5'-RAA YTC NAC RTA RTC NCC YTG-3'<br>SEQ ID NO: 8 |
| Primer 5 | 5'-GTT GGT CAT AAA GGA CAA CG-3'<br>SEQ ID NO: 9 |
| Primer 6 | 5'-TCG GTA TCG TTC AAG AAG TA-3'<br>SEQ ID NO: 10 |
| Primer 7 | 5'-GTN CCN CAY ACN CAY GAY G-3'<br>SEQ ID NO: 11 |
| Primer 8 | 5'-NCA YGA YGA YGT NGG NTG G-3'<br>SEQ ID NO: 12 |
| Primer 9 | 5'-TTG TGG CCA CAC TTT TAC GTC CAG-3'<br>SEQ ID NO: 13 |
| Primer 10 | 5'-CCA TTG CTT CAC GTA ATC TT-3'<br>SEQ ID NO: 14 |
| Primer 11 | 5'-AGC CAT TTC CCG GGA ATG ACC AAA TG-3'<br>SEQ ID NO: 15 |

In the table, mixed base of R = A + G, Y = C + T, and N = A + T + G + C

The cDNA encoding the Dermatophagoides farinae protein of the present invention included an ORF of 3006 bp. The deduced number of amino acids from the DNA sequence was 1002 aa. According to an analysis by a signal sequence predicting software (SignalP 4.1, the initial 27 amino acids constitute a signal peptide. Therefore, the number of amino acids in the Dermatophagoides farinae protein of the present invention as a natural protein is 975 aa, and the molecular weight of the Dermatophagoides farinae protein of the present invention predicted from this amino acid sequence is 113.5 kDa. This predicted molecular weight is consistent with the molecular weight of about 110 kDa indicated by SDS-PAGE.

Homology search of a deduced amino acid sequence from the determined DNA sequence was performed using a BLAST search of NCBI. It indicated that the protein was a novel protein that does not have homology with the known dermatophagoides farinae allergen including Der f 1 and Der f 2.

The invention claimed is:

1. A method for preventing or treating an allergic disease caused by Dermatophagoides farinae, the method comprising administering a Dermatophagoides farinae protein selected from the group consisting of (a), (b) and (c) below, or a fragment peptide comprising 10 to 34 amino acid residues of (a), (b) or (c) below, to a patient in need thereof:
 (a) a protein comprising the amino acid sequence of SEQ ID NO:2;
 (b) a protein comprising an amino acid sequence in which one to ten amino acids have been substituted or deleted, and/or one or several amino acids have been added, relative to the amino acid sequence of SEQ ID NO:2, and having allergenicity of Dermatophagoides farina; and
 (c) a protein comprising an amino acid sequence having 90% or higher identity with the amino acid sequence of SEQ ID NO:2, and having allergenicity of Dermatophagoides farinae.

2. A method for detecting an allergic disease caused by Dermatophagoides farinae, the method comprising administering a Dermatophagoides farinae protein selected from the group consisting of (a), (b) and (c) below, or a fragment peptide comprising 10 to 34 amino acid residues of (a), (b)

or (c) below, to a test subject in need thereof, and measuring an allergic state of the test subject:

(a) a protein comprising the amino acid sequence of SEQ ID NO:2;

(b) a protein comprising an amino acid sequence in which one to ten amino acids have been substituted or deleted, and/or one or several amino acids have been added, relative to the amino acid sequence of SEQ ID NO:2, and having allergenicity of Dermatophagoides farinae; and (c) a protein comprising an amino acid sequence having 90% or higher identity with the amino acid sequence of SEQ ID NO:2, and having allergenicity of Dermatophagoides farina.

3. The method of claim 1, wherein (a) is administered to the patient.

4. The method of claim 1, wherein (b) is administered to the patient.

5. The method of claim 1, wherein (c) is administered to the patient.

6. The method of claim 1, wherein the fragment peptide comprising 10 to 34 amino acid residues of (a), (b) or (c) is administered to the patient.

7. The method of claim 2, wherein (a) is administered to the test subject.

8. The method of claim 2, wherein (b) is administered to the test subject.

9. The method of claim 2, wherein (c) is administered to the test subject.

10. The method of claim 2, wherein the fragment peptide comprising 10 to 34 amino acid residues of (a), (b) or (c) is administered to the test subject.

\* \* \* \* \*